United States Patent
Hod et al.

(10) Patent No.: US 9,381,014 B2
(45) Date of Patent: Jul. 5, 2016

(54) SURGICAL FASTENER HAVING A SNAP LOCK AND DEVICES DEPLOYING IT

(75) Inventors: Eitan Hod, Zichron Ya'akov (IL); Matan Gedulter, Yesod Hama'alah (IL)

(73) Assignee: I.B.I. ISRAEL BIOMEDICAL INNOVATIONS LTD., Caesarea Industrial Park (IL)

( * ) Notice: Subject to any disclaimer, the term of this patent is extended or adjusted under 35 U.S.C. 154(b) by 102 days.

(21) Appl. No.: 14/343,248

(22) PCT Filed: Sep. 13, 2012

(86) PCT No.: PCT/IL2012/050363
§ 371 (c)(1),
(2), (4) Date: Mar. 6, 2014

(87) PCT Pub. No.: WO2013/038410
PCT Pub. Date: Mar. 21, 2013

(65) Prior Publication Data
US 2014/0222028 A1    Aug. 7, 2014

Related U.S. Application Data

(60) Provisional application No. 61/535,019, filed on Sep. 15, 2011.

(51) Int. Cl.
*A61B 17/064* (2006.01)
*A61B 17/076* (2006.01)
*A61B 17/04* (2006.01)
(Continued)

(52) U.S. Cl.
CPC ........... *A61B 17/064* (2013.01); *A61B 17/0401* (2013.01); *A61B 17/068* (2013.01); *A61B 17/0643* (2013.01); *A61B 17/0644* (2013.01); *A61B 17/076* (2013.01); *A61B 2017/0641* (2013.01); *A61F 2002/0072* (2013.01)

(58) Field of Classification Search
CPC .......... A61B 17/0401; A61B 17/0644; A61B 17/064; A61B 17/0643; A61B 17/068; A61B 17/076; A61B 2017/0641; A61F 2002/0072
USPC .................. 606/139, 142, 151, 155, 157, 178
See application file for complete search history.

(56) References Cited

U.S. PATENT DOCUMENTS 5,156,609 A * 10/1992 Nakao ................ A61B 17/0682
227/179.1
5,470,010 A 11/1995 Rothfuss et al.
(Continued)

FOREIGN PATENT DOCUMENTS

EP        1908420        4/2008

OTHER PUBLICATIONS

International Search Report and Written Opinion from International Application No. PCT/IL2012/050363 mailed Nov. 28, 2012.

*Primary Examiner* — Jing Ou
(74) *Attorney, Agent, or Firm* — Dorsey & Whitney LLP

(57) ABSTRACT

A surgical fastener having a top element including a crown, with prongs extending from the crown. A baseplate having two or more slots that are dimensioned to receive a tip of a prong in the undeployed configuration of the fastener. Two or more cantilevered catches extend from the crown, each cantilevered beam terminating in a head. The baseplate is provided with a bore and in the deployed configuration, the catches of the top element pass through the bore and latch the top element onto the baseplate.

20 Claims, 17 Drawing Sheets

(51) Int. Cl.
*A61B 17/068* (2006.01)
*A61F 2/00* (2006.01)

(56) References Cited

U.S. PATENT DOCUMENTS

| | | | |
|---|---|---|---|
| 5,582,616 A | 12/1996 | Bolduc et al. | |
| 5,766,189 A * | 6/1998 | Matsuno | A61B 17/128 606/139 |
| 5,810,882 A | 9/1998 | Bolduc et al. | |
| 5,830,221 A | 11/1998 | Stein et al. | |
| 6,666,873 B1 | 12/2003 | Cassell | |
| 7,011,667 B2 * | 3/2006 | Kobayashi | A61B 17/1285 606/139 |
| 7,740,639 B2 * | 6/2010 | Hummel | A61B 17/122 606/139 |
| 7,806,903 B2 * | 10/2010 | Shibata | A61B 17/083 600/104 |
| 8,262,678 B2 * | 9/2012 | Matsuoka | A61B 17/1227 606/139 |
| 8,419,751 B2 * | 4/2013 | Harada | A61B 17/122 606/139 |
| 9,050,163 B2 * | 6/2015 | Goldberg | A61B 17/11 |
| 2002/0058955 A1 | 5/2002 | Blatter et al. | |
| 2004/0133221 A1 | 7/2004 | Sancoff et al. | |
| 2009/0182352 A1 | 7/2009 | Paz et al. | |
| 2009/0264900 A1 | 10/2009 | Paz et al. | |

* cited by examiner

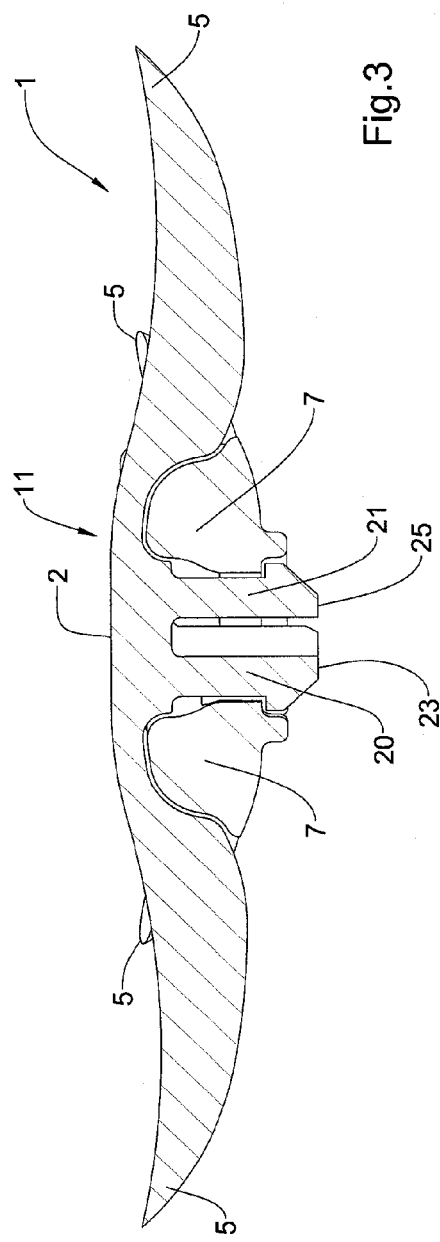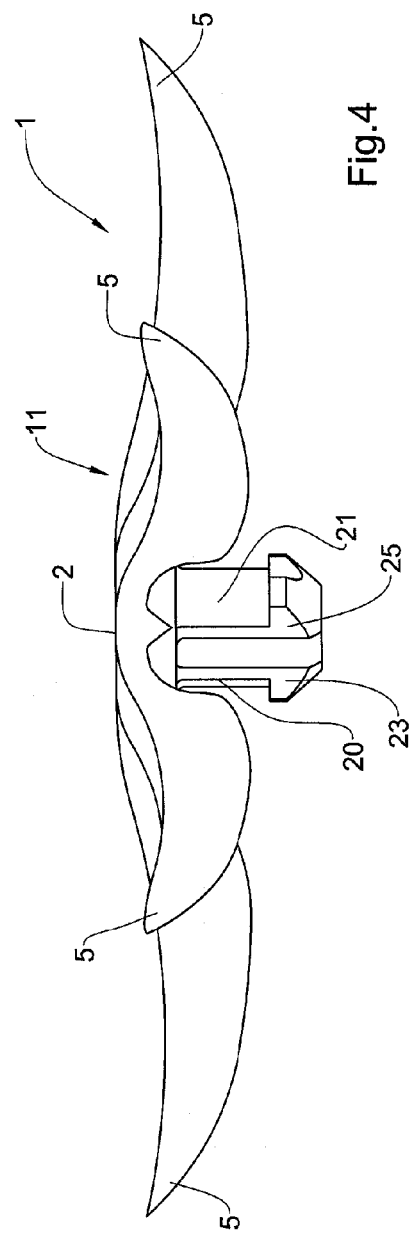

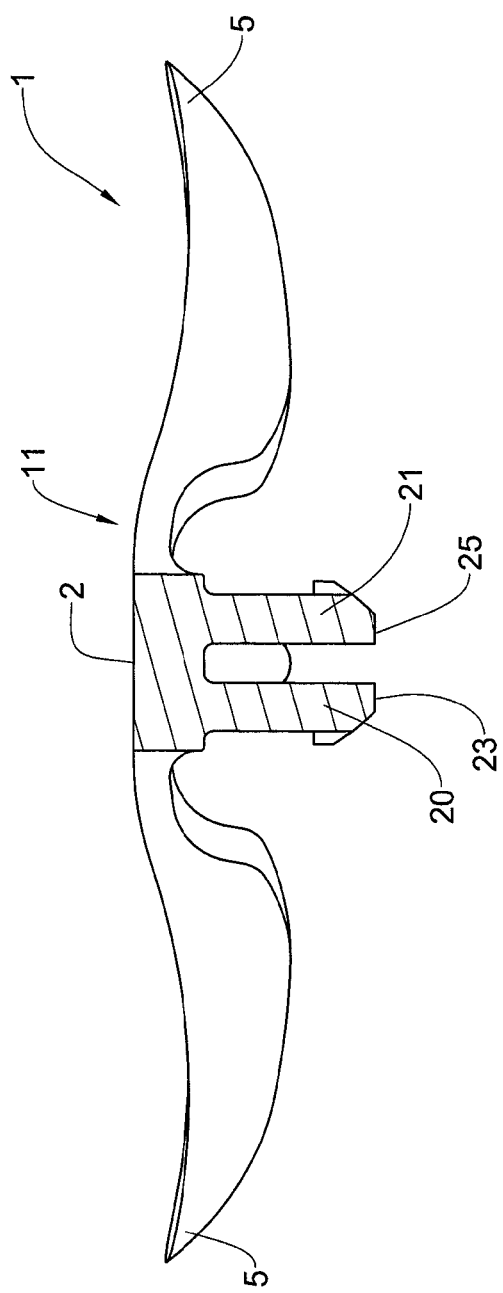

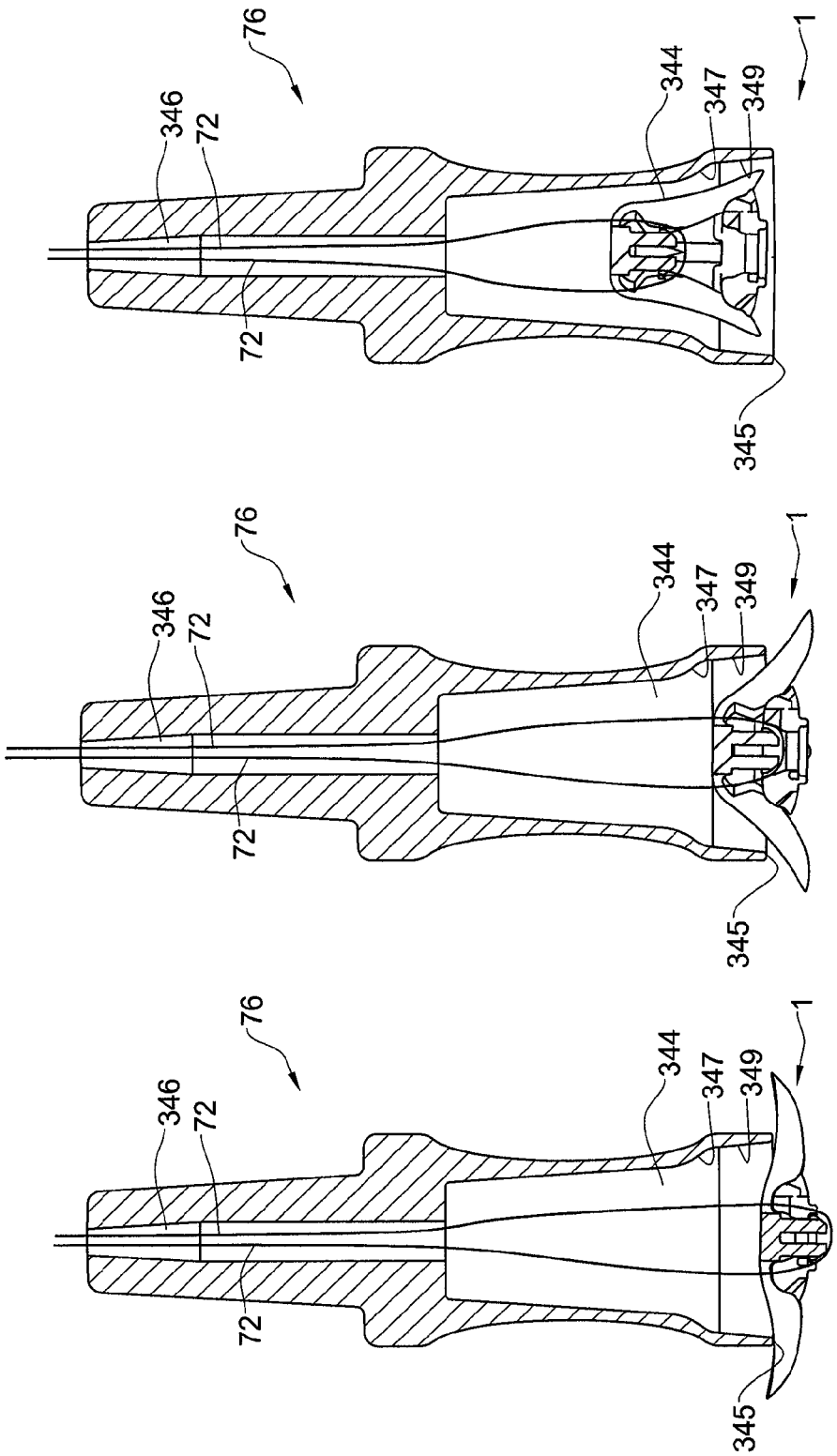

SURGICAL FASTENER HAVING A SNAP LOCK AND DEVICES DEPLOYING IT

FIELD OF THE INVENTION

This invention relates to surgical fasteners and to surgical fastening devices.

BACKGROUND OF THE INVENTION

Surgical anchors are used instead of surgical suturing, which is often both time consuming and inconvenient, in order to join two tissue locations. A surgeon can often use a stapling apparatus to implant an anchor into a body tissue and thus accomplish in a few seconds, what would take a much longer time to suture. A surgical anchor is used, for example in inguinal hernia surgery to fasten polypropylene mesh to the abdominal wall in order to reinforce the abdominal wall.

Conventional surgical fasteners have been in the form of ordinary metal staples, which are bent by the delivery apparatus to join together body tissues. These staples comprise a pair of legs or prongs joined together at one end by a crown that may be straight or arcuate. During deployment of the staple, the prongs are inserted into a tissue and are then made to bend inwards towards.

At present, there are a variety of surgical fasteners and fastening devices available for endoscopic or open procedures, to attach tissues together, or to attach a mesh patch to a tissue. One such surgical fastener is a surgical stapler, or clip applicator. In this stapler, a plurality or stack of unformed staples are contained within a cartridge and are sequentially advanced or fed within the instrument by a spring mechanism. A secondary feeding mechanism is employed to separate the distal most staple from the stack, and to feed the distal most stapler into the staple closing mechanism. Such mechanisms are found in U.S. Pat. Nos. 5,470,010, and 5,582,616.

In some applications, the body tissue is accessible from two opposite direction so that an anvil may be used to deform the legs of a staple after having passed through the body tissue. In applications where access to the tissue is from only one direction, an anvil may be used to deform the crown of a conventional staple so that the legs project towards each other in the body tissue so as to hold the staple in the tissue.

Another stapler mechanism, used mostly for mesh attachment to tissue does not use an anvil. Instead, a fastener comprising a helical wire is screwed or rotated into a tissue, in order to join tissues to affix a polypropylene or similar material mesh or other patch to the tissue together. Instruments and fasteners of this type are found in U.S. Pat. Nos. 5,582,616, 5,810,882, and 5,830,221. Another type of fastener that does not need an anvil applies fasteners made from a shape memory alloy such as Nitinol™. These fasteners are mainly used to fasten prosthetic material or artificial mesh to tissue.

These fasteners and fastening devices suffer from significant drawbacks especially when attaching fasteners to soft tissue. The strength of attachment of these devices depends mainly on the content and size of collagen fibers. Most soft tissue, such as subcutaneous tissue and fatty tissue surrounding internal organs, has few and slender collagen fibers and hence the attachment of the common art fasteners to such tissue is weaker than attachment to stronger tissues such as fascia or ligaments, which have more and larger collagen fibers.

SUMMARY OF THE INVENTION

In its first aspect, the present invention provides a surgical fastener. The fastener of the invention comprises a top element consisting of a crown from which two or more prongs extend, and a baseplate. In the undeployed configuration of the fastener, the crown is separated from the baseplate with the tip of each prong being immobilized in a slot of the baseplate. A pair of cantilevered catches that terminate in a beveled head extend from below the crown. During deployment of the fastener, the crown is urged towards the baseplate. As the crown approaches the baseplate, the prongs pass through the slots and splay radially outward from the crown to attain the deployed configuration. As the fastener attains the deployed configuration, the cantilevered catches pass through a central bore in the base plate and then latch the top element onto the baseplate to lock the fastener in its deployed configuration.

Thus, in one aspect, the invention provides a surgical fastener having an undeployed configuration and a deployed configuration, comprising:

(a) a top element including a crown, there being two or more prongs extending from the crown;

(b) a base plate having two or more slots, each slot being dimensioned to receive a tip of a prong of the top element in the undeployed configuration of the fastener;

wherein two or more cantilevered catches extend from the crown, each cantilevered beam terminating in a head;

wherein the baseplate is provided with a bore;

wherein in the deployed configuration the catches of the top element pass through the bore and latch the top element onto the baseplate.

and wherein in the undeployed configuration, the catches do not latch the top element to the baseplate.

In the surgical fastener of the invention, in the undeployed configuration, each prong may be immobilized in a slot by frictional forces between the prong and a wall of the slot.

In the surgical fastener of the invention, at least one head may be beveled.

In the surgical fastener of the invention, the prongs may splay out radially when the fastener goes from the undeployed configuration to the deployed configuration.

In the surgical fastener of the invention, the crown may have a shape of a disk, a rectangular or polygonal shape, or an irregularly shaped surface. The baseplate may have a shape of a disk, a rectangular or polygonal shaped surface, or an irregularly shaped surface. The prongs may have a rectangular profile, a round profile, an oval profile, a triangular profile, or an elliptical profile. The prongs may have a blunt tip, a pointed tip or a barbed tip. The surgical fastener of the invention may be manufactured from a biodegradable material.

In the surgical fastener of the invention, may further comprise a filament passing between the top element and the baseplate. A ring may be attached to ends of the filament. The fastener in this case may further comprise a bell shaped extractor, with the filament passing through the extractor.

The invention also provides a system comprising one or more surgical fasteners of the invention and a surgical fastening device configured to bring a surgical fastener according to any one of the previous claims from the undeployed configuration to the deployed configuration. The fastening device may comprise a shaft extending from a handle portion, the shaft having a distal end provided with radially inward projections. The shaft of the surgical fastening device may be detachable from the handle portion. The shaft may be provided with axial protrusions configured to grasp a mesh material.

In the system of the invention, the surgical fastening device may further comprise a trigger and a pusher, and wherein squeezing the trigger against the handle portion causes the pusher to move distally inside a lumen of the shaft to eject the fastener from the distal end of the shaft as the fastener attains its deployed configuration.

The distal end of the shaft may be configured to receive a surgical fastener that is loaded into a holder to form an assembly. In this case, the system may further comprise a holder configured to be loaded with a surgical fastener of the invention. The system may also comprise a cartridge configured to receive the assembly.

The invention also provides a system comprising one or more surgical fasteners of the invention and an extraction device, the extraction device having an internal passageway shaft that terminates in a lumen, the lumen being configured to receive the top element of a fastener of the system, the lumen further having a rim dimensioned to allow the prongs of a fastener of the system to abut the rim when the top element of the fastener is positioned in the lumen of the extraction device.

BRIEF DESCRIPTION OF THE DRAWINGS

In order to understand the invention and to see how it may be carried out in practice, embodiments of the invention will now be described by way of non-limiting example only, with reference to the accompanying drawings, in which:

FIG. 3 shows a sectional view of the fastener of FIG. 2 in the deployed configuration;

FIG. 4 shows the top element of the surgical fastener of FIG. 1 in the deployed configuration in a perspective side view;

FIG. 5 shows the top element of the surgical fastener of FIG. 1 in the deployed configuration in a sectional view;

FIGS. 16a to 16c show extraction of a surgical fastener from a body tissue using one embodiment of an extraction device;

DESCRIPTION OF EMBODIMENTS

Figure 1:
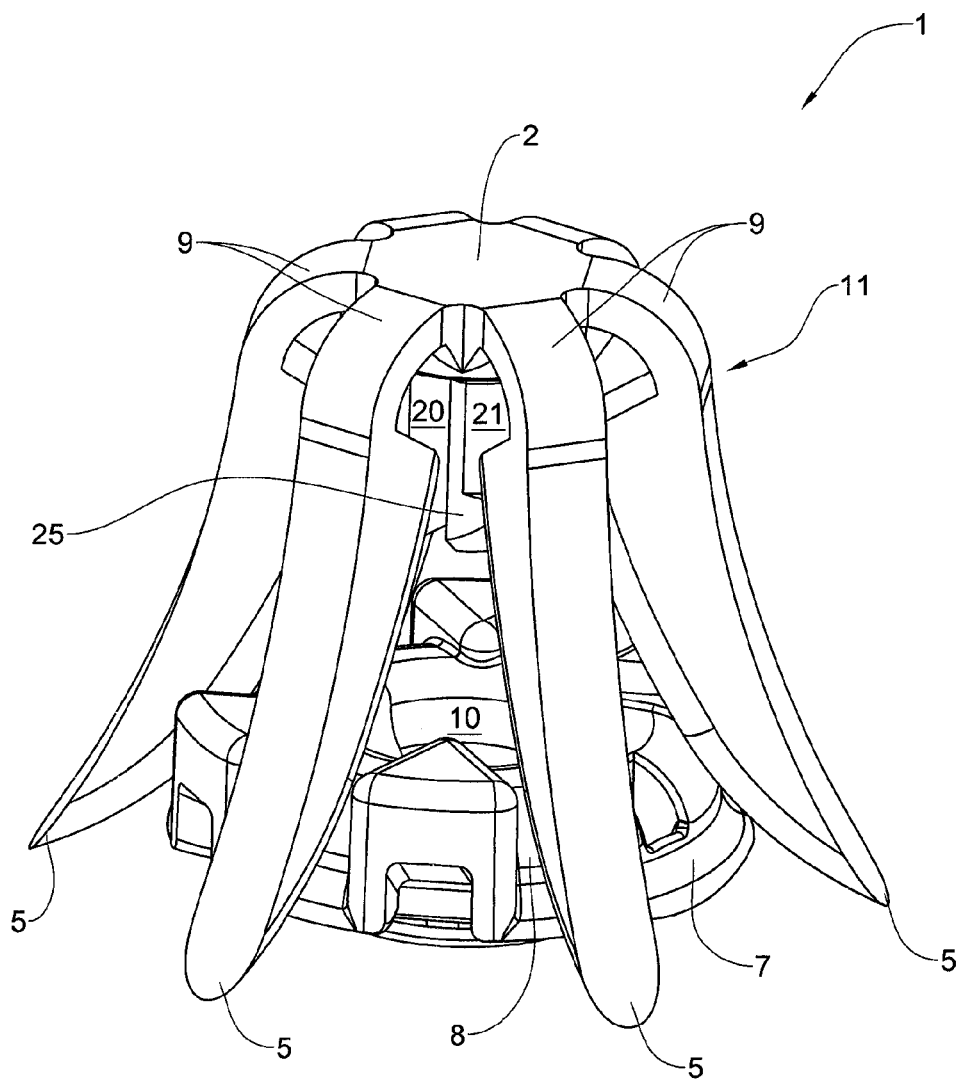
FIG. 1 shows a perspective view of a surgical fastener in an undeployed configuration in accordance with one embodiment of the invention.
Figure 2:
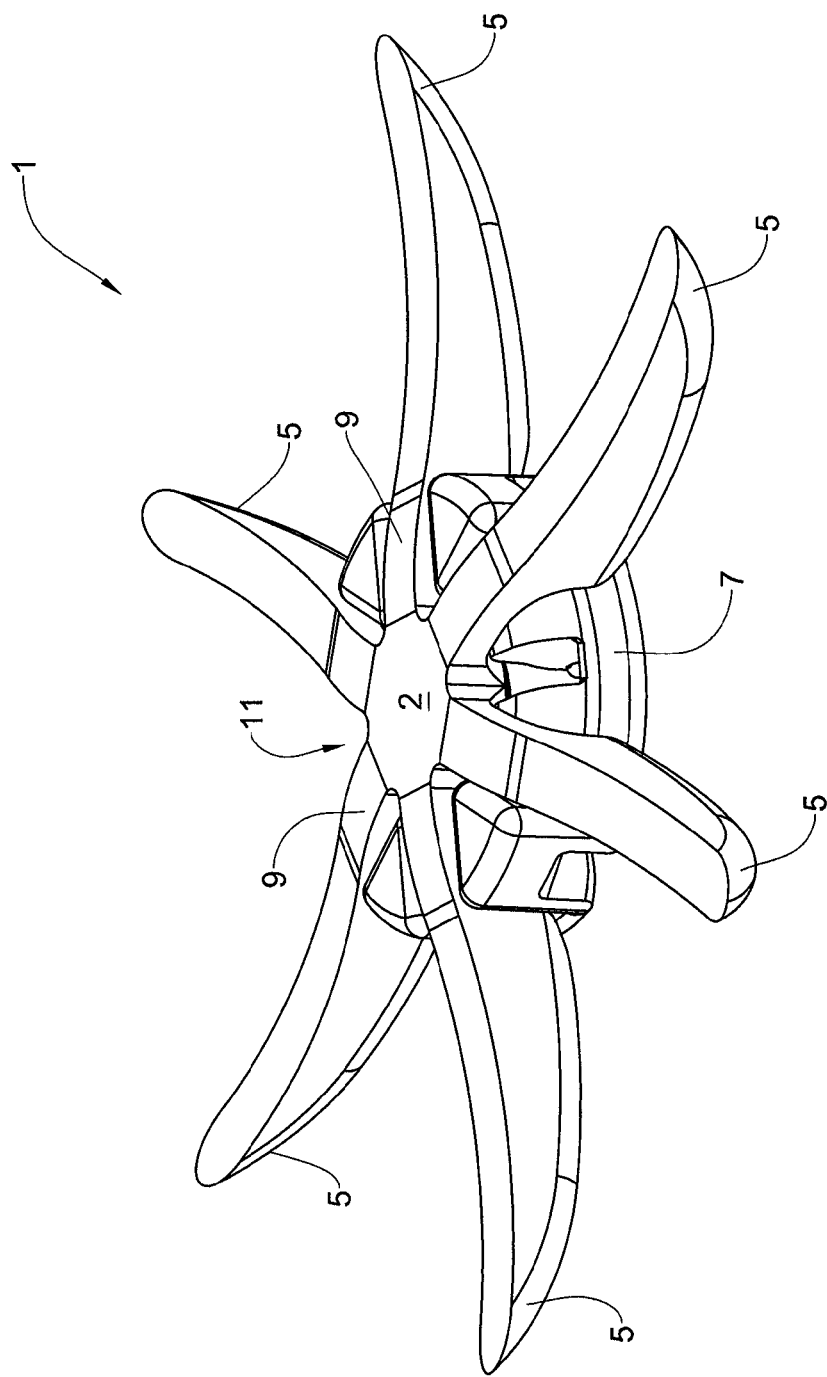
FIG. 2 shows a perspective view of the surgical fastener of FIG. 1 in a deployed configuration.

FIGS. 1 to 3 show a surgical fastener 1 in accordance with one embodiment of the invention. The fastener 1 in its undeployed configuration is shown in a side perspective view in FIG. 1. The fastener 1 in its deployed configuration is shown in a side perspective view in FIG. 2. A cut away sectional view of the deployed configuration of the fastener 1 is shown in FIG. 3. The fastener 1 comprises a top element 11 consisting of a crown 2 from which two or more prongs 5 extend, and a baseplate 7. The top element 11 in the deployed configuration is shown alone in a side view in FIG. 4 and in a cross sectional view in FIG. 5. The baseplate 7 is shown alone in a perspective view in FIG. 6.

The baseplate 7 has a central bore 10 from which extend two or more slots 8 to an edge of the baseplate 7. The prongs 5 and the slots 8 are dimensioned so that in the undeployed configuration of the fastener (FIG. 1), each prong is immobilized in a slot by frictional forces between the prong and the wall of the slot.

Figure 6:
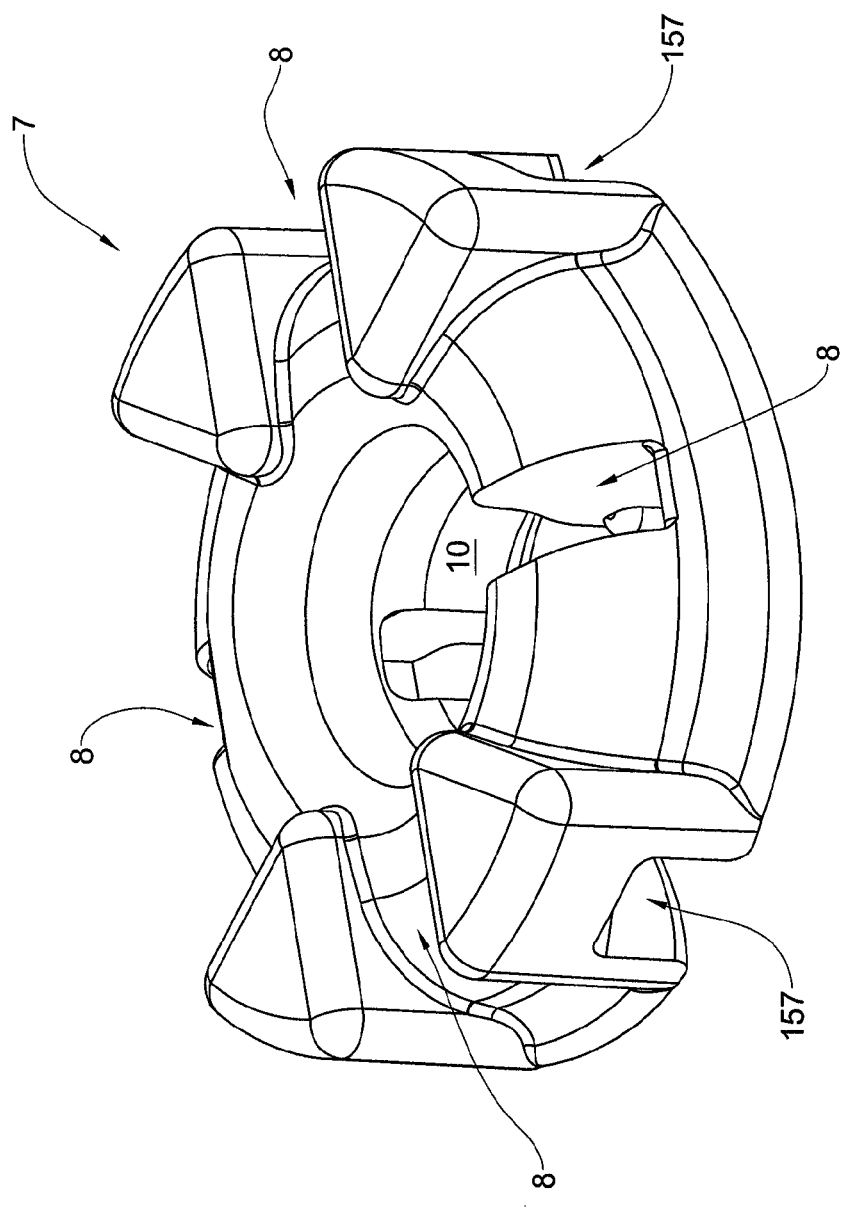
FIG. 6 shows the baseplate of the surgical fastener of FIG. 1.

A pair of cantilevered catches 20 and 21 that terminate in beveled heads 23 and 25 extend from below the crown 2 (best seen in FIGS. 4 and 6). During deployment of the fastener 1, a fastening device is used on the fastener in the undeployed configuration that urges the crown 2 towards the baseplate 7, as described in detail below. As the prongs pass through the slots 8, the force applied to the prongs 5 by the slots 8 causes a curved region 9 of each prong to straighten as the prongs splay radially outward from the crown to attain the deployed configuration (FIGS. 2 and 4). As the fastener attains the deployed configuration, the cantilevered beams 20 and 21 enter the bore 10 in the base plate. As the heads 23 and 25 pass through the bore 10, the cantilevered catches 20 and 21 are displaced inwards until the heads 23 and 25 have completely passed through the bore 10. The cantilevered catches 20 and 21 are then free to snap outwards to retain their original straight configuration. The top element 11 thus becomes latched onto the baseplate 8 so that the fastener 1 is locked in its deployed configuration, as shown in FIG. 3.

The crown and baseplate may have any shape, as required in any application. For example, the crown may have a shape of a disk, a rectangular or polygonal shape, an irregularly shaped surface. The baseplate may have a shape of a disk, a rectangular or polygonal shaped surface, an irregularly shaped surface.

The top element 2 may contain any number of prongs 5 that is at least two. The prongs may have any profile as required in any application, such as a rectangular profile, a round profile, an oval profile, a triangular profile, or an elliptical profile. The prongs may be straight or curved with constant or variable curvature. The prongs may have blunt tips, pointed tips or barbed tips, as required in any application.

The fastener of the invention may be manufactured from any biocompatible, and preferentially biodegradable, materials such as but not limited to: PLA, PLGA, poly-caprolactone, polydiaxone, stainless steel, magnesium alloys or any combination of such materials.

Figure 7:
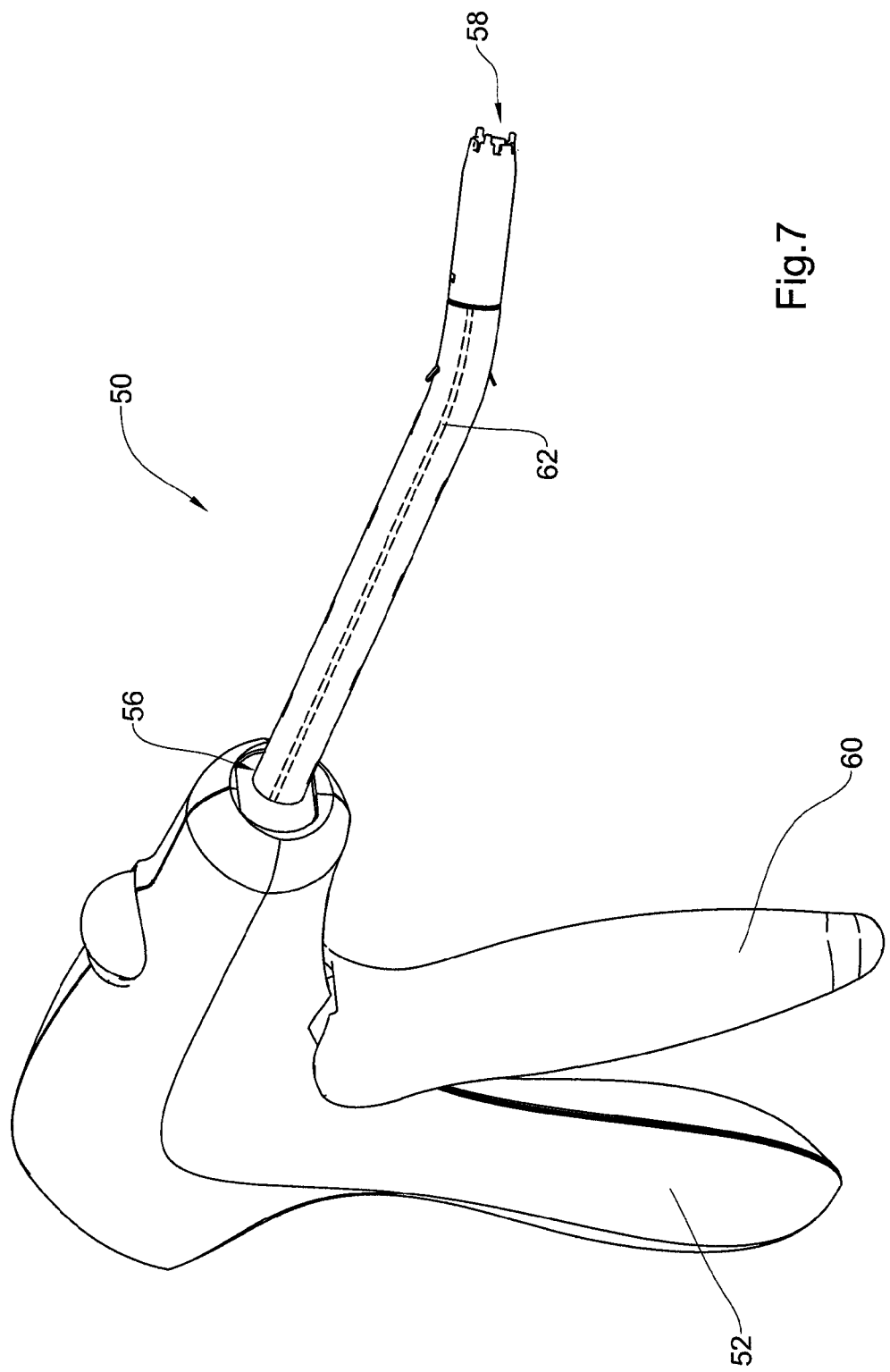
FIG. 7 shows a surgical fastening device in accordance with one embodiment of the invention.

FIG. 7 shows a surgical fastening device 50 in accordance with one embodiment of this aspect of the invention. The fastening device 50 is used to deploy a surgical fastener of the invention having a top element and baseplate, such as the fastener 1 shown in FIGS. 1 and 2. The fastening device 50 of the invention may be manufactured from biocompatible materials, such as biocompatible metallic or plastic materials, or a combination of them.

Figure 8:
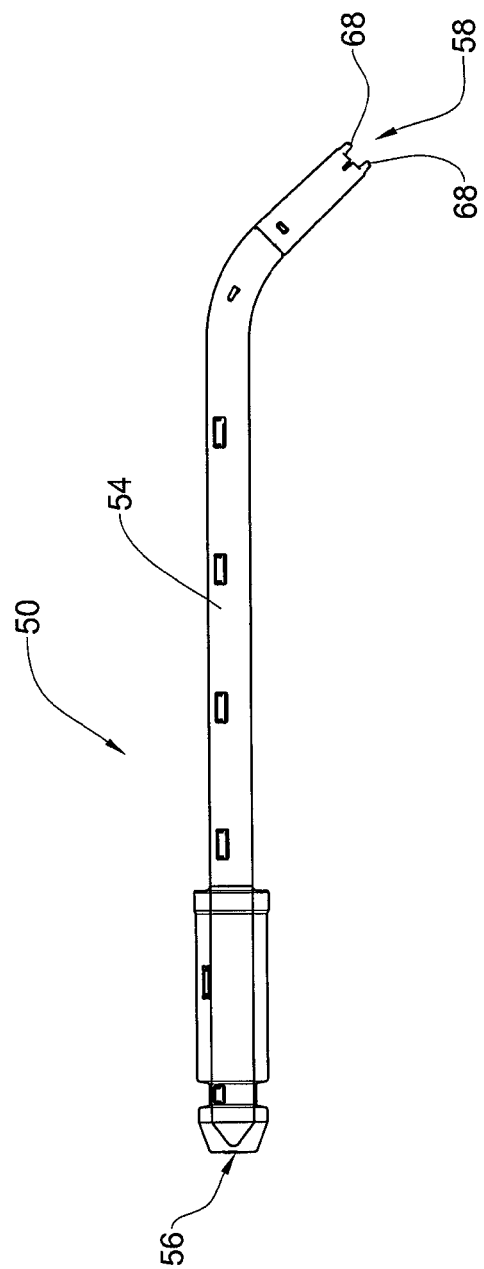
FIG. 8 shows a side view of the shaft of the surgical fastening device of FIG. 7.
Figure 9:
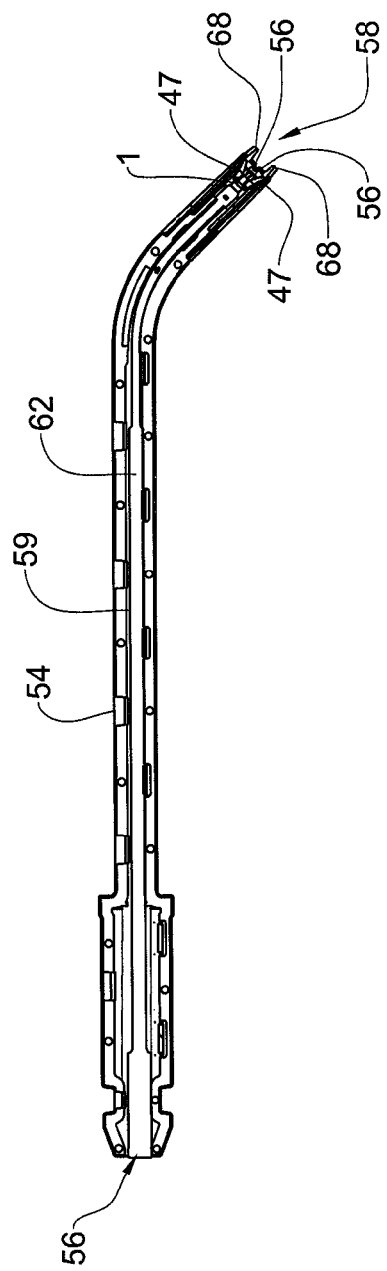
FIG. 9 shows longitudinal sectional view of the shaft of FIG. 8.

The fastening device 50 is provided with a handle portion 52 from which extends a slender shaft 54 having a proximal end 56 and a distal end 58. The shaft 54 may be detachable from the handle portion 52. The detached shaft 54 is shown in a side view in FIG. 8, and in a longitudinal sectional view in FIG. 9. The shaft of the deployment device may be straight or curved; rigid, semi-rigid or flexible. It may be flexible along its entire length or only at specific locations thus permitting manipulation of the shaft in narrow body spaces. The shaft 54 may be bent near its distal end 58 and can be rotated in the handle portion 52 in order to direct the distal end 58 of the shaft 54 in any desired direction to facilitate positioning of the distal end 58 at a desired body location. The distal end 58 of the shaft 54 is provided with longitudinal grippers 47 each of which is provided with a radially inward projection 56 at its tip. The shaft 54 may be provided at its distal end with axial protrusions 68 that are used to grasp a mesh material in order to bring it to a desired position on a tissue surface when a mesh is to be attached by a fastener of the invention. As shown in FIG. 9, a fastener 1 of the invention in its undeployed configuration is loaded into the distal end of the shaft and is held in place by the grippers 47. Squeezing a trigger 60 against the handle portion 52 causes a pusher 62 to move distally inside a lumen 59 of the shaft to eject the fastener from the distal end 58 as the fastener attains its deployed configuration.

Figure 12:
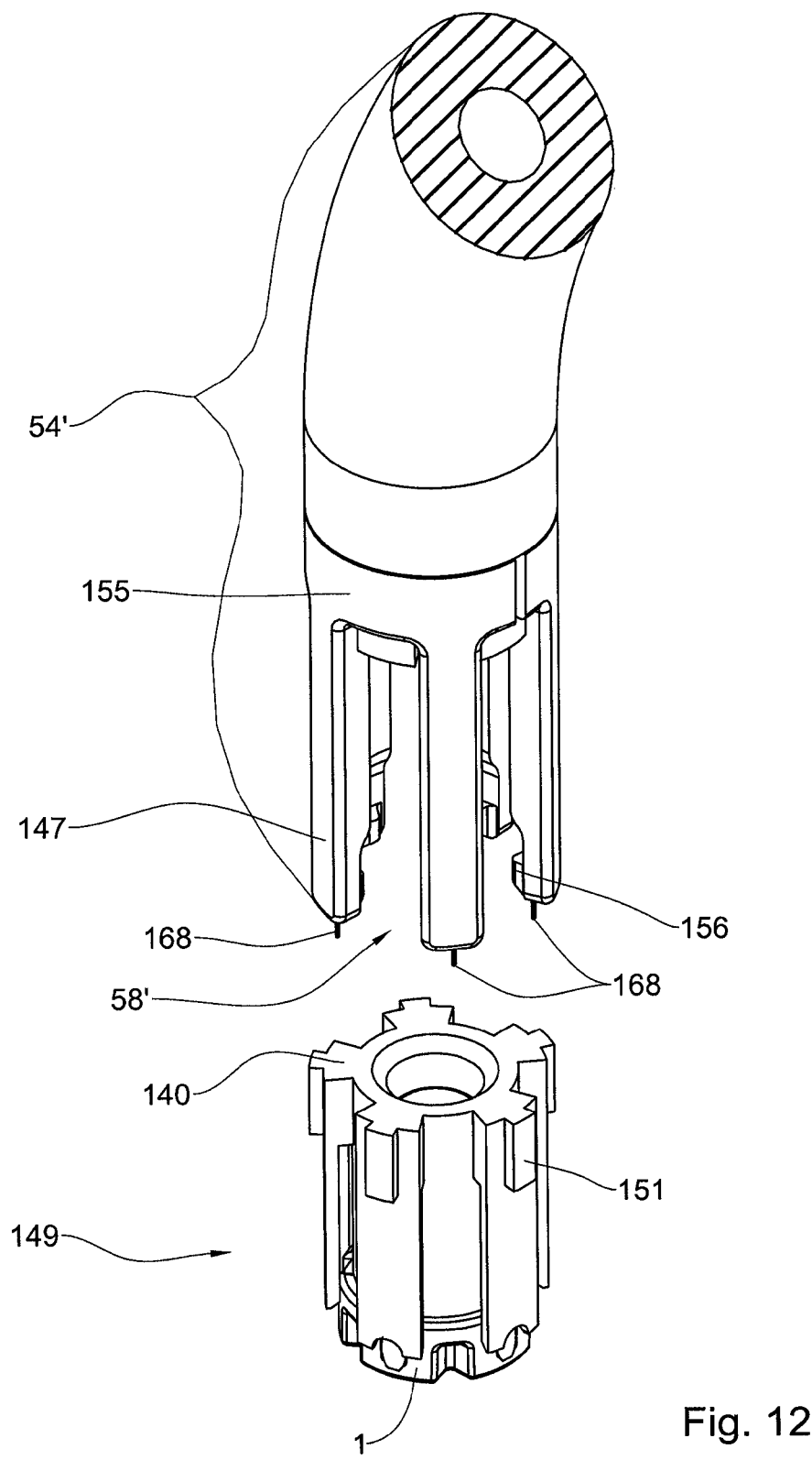
FIG. 12 shows an enlarged view of the distal end of the shaft of the fastening of FIG. 18 and the assembly of FIG. 11.
Figure 18:
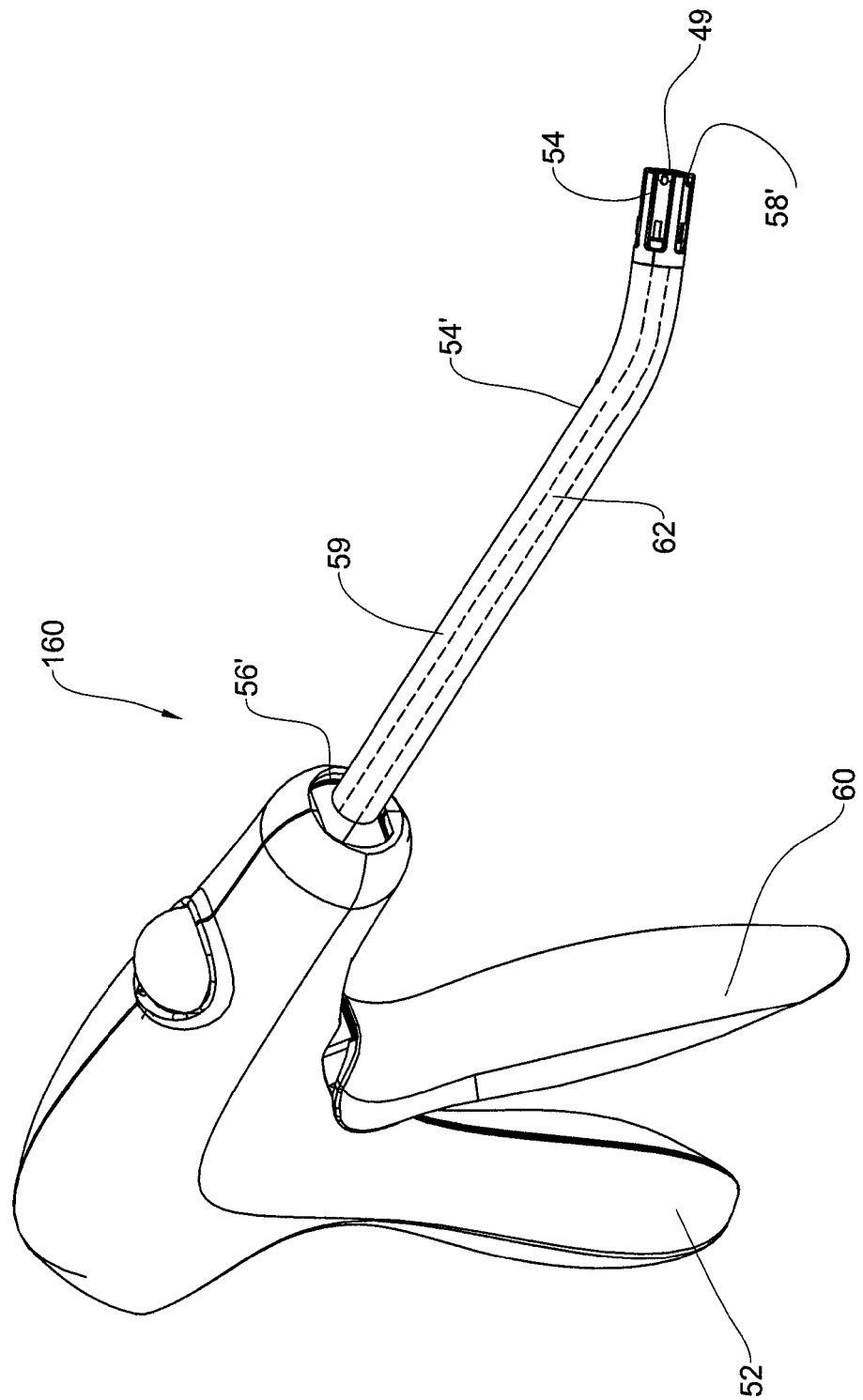
FIG. 18 shows a surgical fastening device in accordance with another embodiment of the invention.

FIG. 18 shows a fastening device 160 for deploying a surgical fastener of the invention in accordance with another embodiment of the invention. The fastening device 160 has many components in common with the fastening device 50 shown in FIG. 7, and similar components are indicated with the same reference numeral without further comment. The fastening device 160 has a shaft 54' having a proximal end 56' and a distal end 58'. The distal end 58' of the shaft 54' is shown in greater detail in FIG. 12. The distal end 58' is configured to receive a fastener 1 of the invention that has been preloaded into a holder 140 to form an assembly 149. The distal end 58' of the shaft 54' is provided with a rim 155 with longitudinal grippers 147 each of which is provided with a radially inward projection 156 at its tip. The distal end 58' may be provided with axial protrusions 168 that are used to grasp a mesh material in order to bring it to a desired position on a tissue surface when a mesh is to be attached by a fastener of the invention.

Figure 10A:
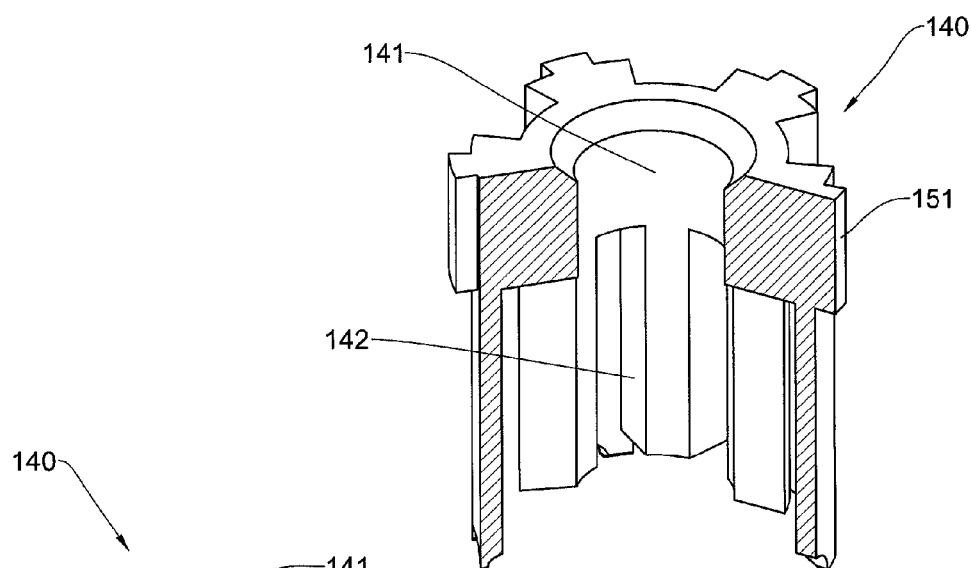
FIG. 10 shows a holder for a fastener of the invention.
Figure 10B:
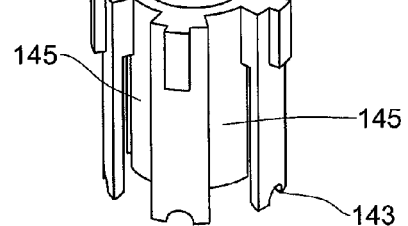
Figure 10C:
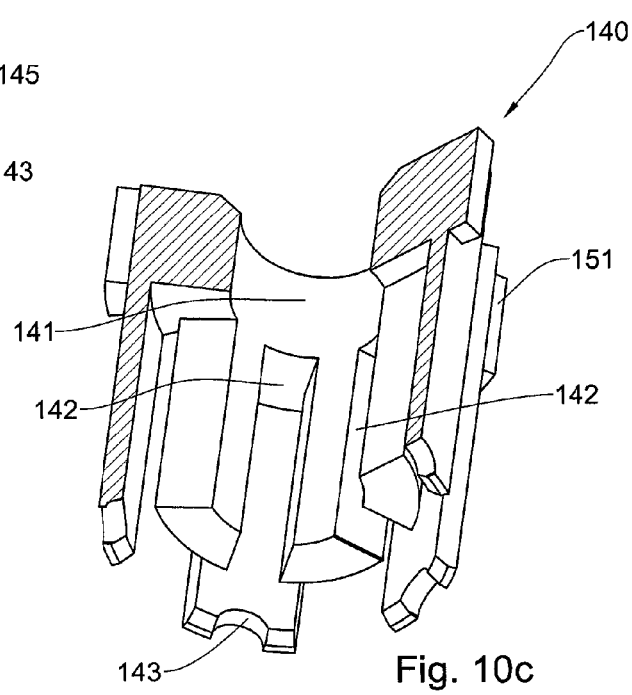
Figure 11:
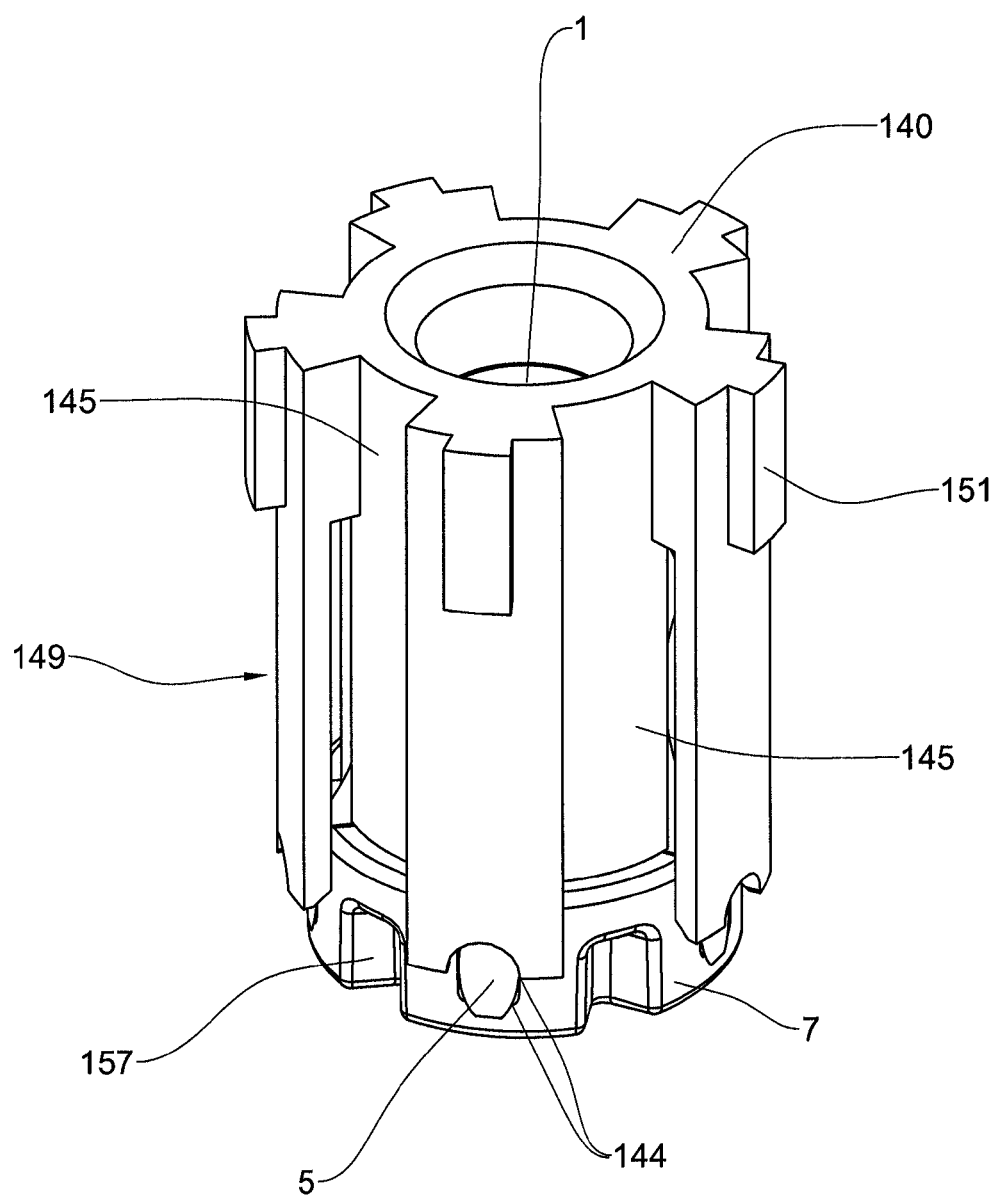
FIG. 11 shows an assembly comprising the undeployed fastener and the holder of FIG. 10.

As shown in FIGS. 10a to 10c, the holder 140 is essentially cylindrical and comprises a central bore 141 configured to receive the undeployed fastener. The central bore 141 is provided with radially disposed recesses 142 for retaining the prongs 5 of the fastener along the longitudinal axis of the undeployed fastener. FIG. 11 shows the assembly 149 comprising the undeployed fastener 1 and the holder 140. When the holder 140 is mounted on the fastener 1 in the undeployed configuration of the fastener, notches 143 in the holder 140 are aligned with the slots 8 of the baseplate to form channels 144. As explained below, the channels 144 house and guide the prongs 5 during splaying and deployment.

Figure 13:
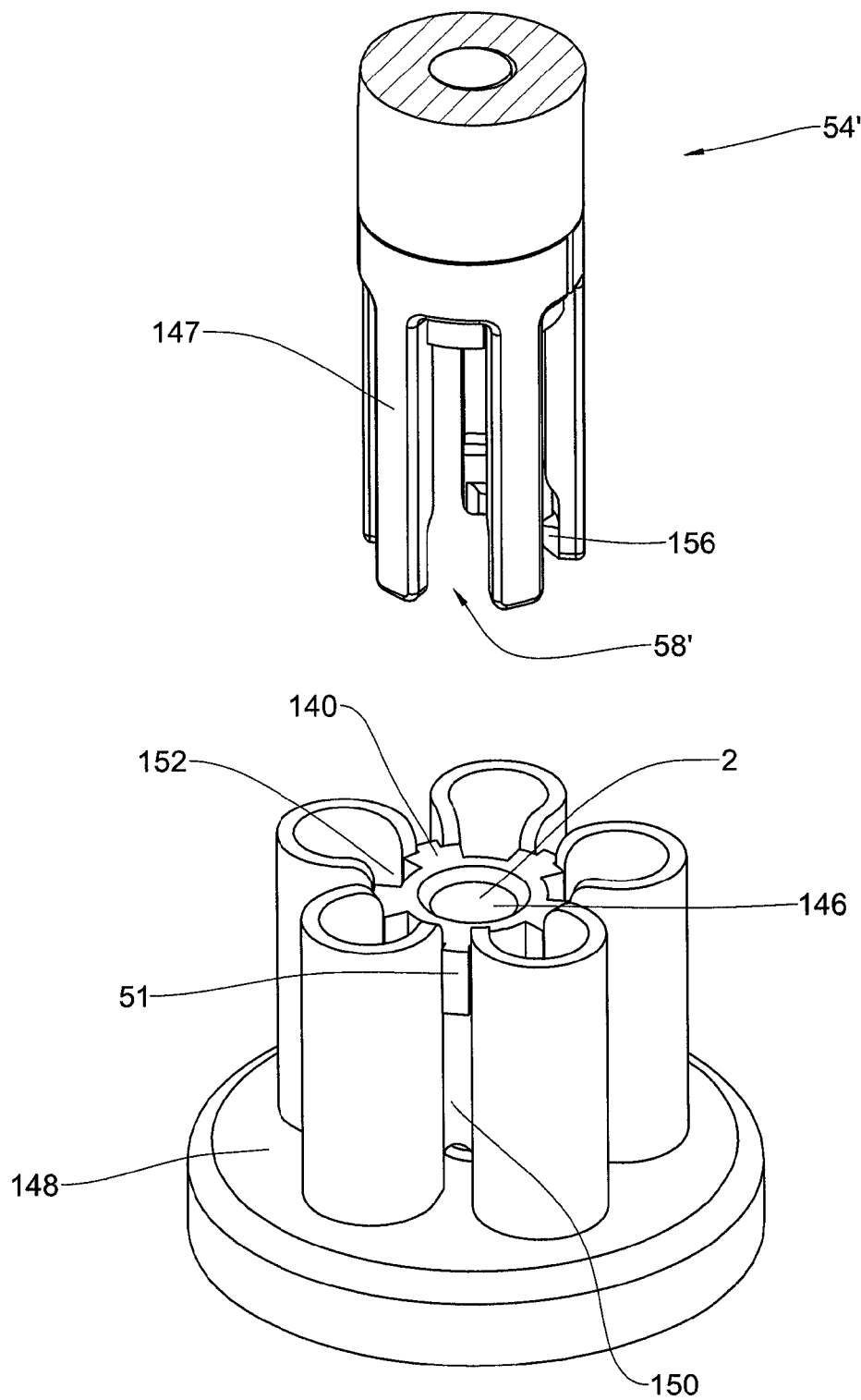
FIG. 13 shows insertion of the assembly of FIG. 11 into a cartridge.

The assembly 149 is inserted into a cartridge 148, shown in FIG. 13. The cartridge 148 has a central bore 146 that is provided with longitudinal recesses 150 that mate with longitudinal projections 151 on the outer surface of the holder 140. When the assembly 149 is introduced into the central bore of the cartridge 148, additional longitudinal recesses 152 of the cartridge 148 mate with longitudinal grippers 147 situated at the distal end of a fastening device 160 (FIG. 18), as explained below.

Figure 14:
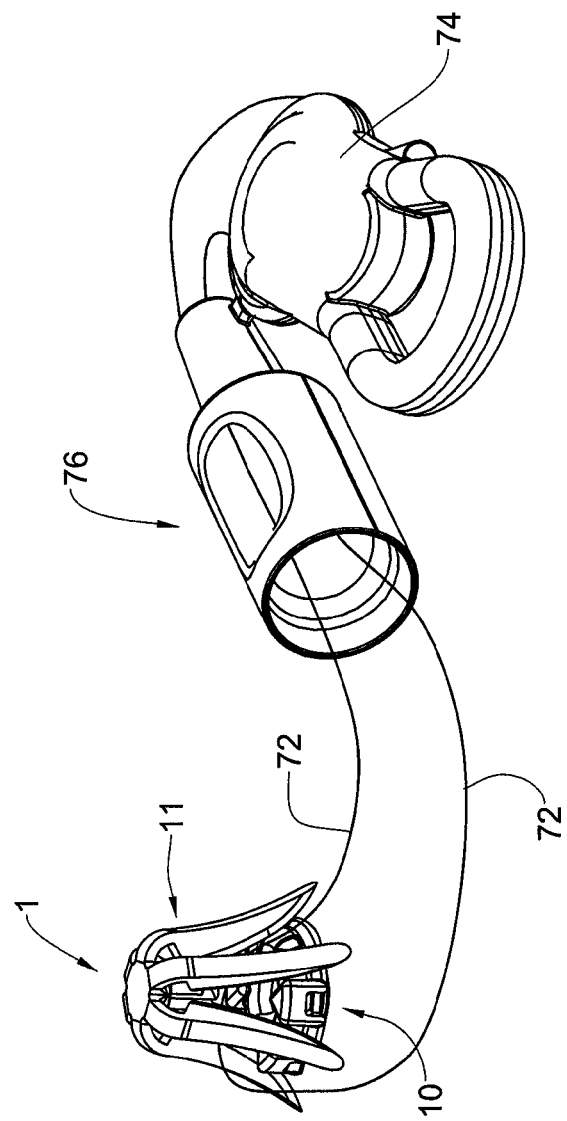
FIG. 14 shows a fastener of the invention mounted onto the fastening device of FIG. 7 together with an extraction device.

Referring still to FIG. 13, in order to mount the assembly 149 when placed in the cartridge 148 onto the distal end 54 of the fastening device 50, the grippers 147 of the distal end 154 are introduced into the mating recesses 152 of the cartridge 148 and into the recesses 145 of the holder 140. The projection 156 at the tip of the grippers 147 engages small fitting recesses 157 of the baseplate 7 (see FIG. 1). In this way, the undeployed fastener 1, in the assembly 149, is engaged in the distal end 58' by the projections 156 of the grippers 147. The assembly 149 comprising the fastener 1 and the holder 140 can then be removed from the cartridge 148. FIG. 14 shows the shaft 54 after mounting of the fastener 1.

The fastener 1 may be provided with an extraction device that is used to extract the fastener after deployment of the fastener when deployment of the fastener is not satisfactory. One embodiment of the extraction device is shown in FIG. 14. The extraction device includes a filament 72 that is passed between the top element 11 and the baseplate 10 prior to mounting the fastener 1 onto the fastening device. The ends of the filament 72 are attached to a ring 74. Two courses of the filament 72 pass though a bell shaped extractor 76. As explained below, the filament facilitates removal of the fastener from a body tissue.

Figure 15A:
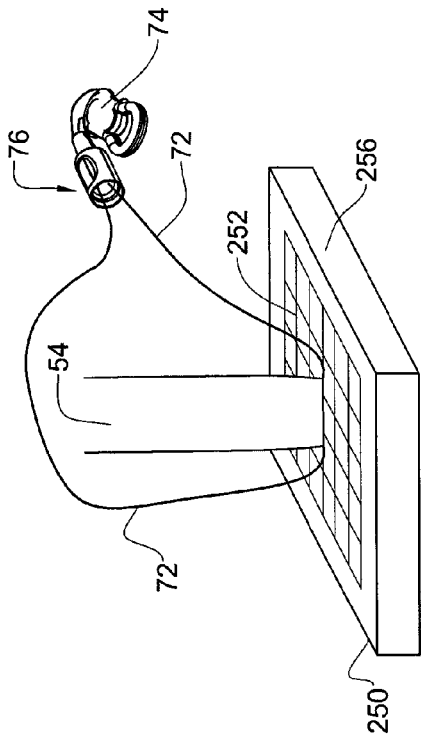
FIGS. 15a to 15d show mounting of a piece of mesh to the distal end of the shaft of the fastening device of FIG. 7 and fastening the mesh to a tissue surface.
Figure 15B:
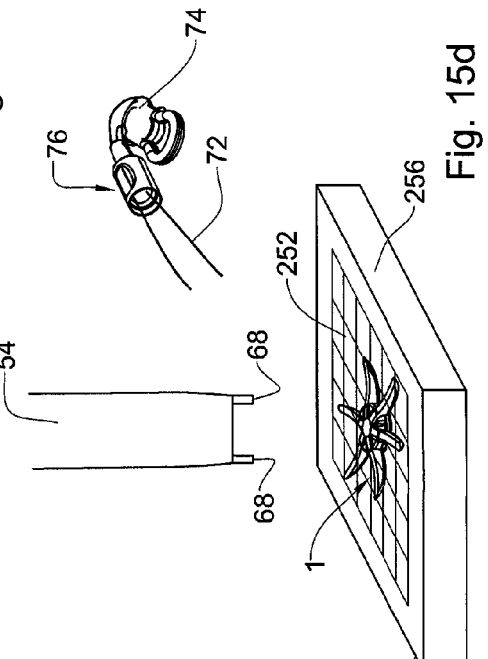
Figure 15C:
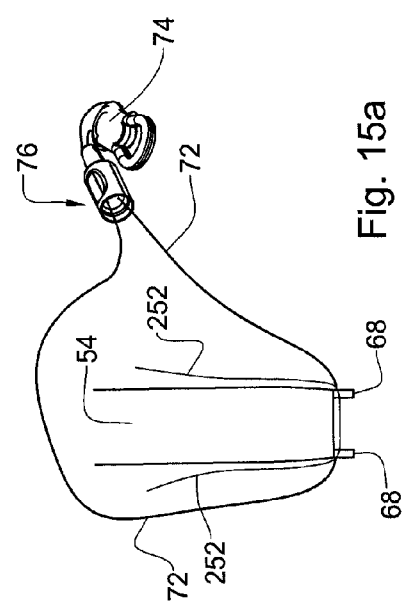

Deployment of a fastener 1 of the invention will now be described using the fastening device 50 shown in FIG. 7, deployment of the fastener 1 with the fastening device 160 shown in FIG. 18 being essentially the same. As shown in FIG. 15a, a piece of mesh 252 may be mounted onto the axial projections 68 on the distal end of the shaft. Then, as shown in FIG. 15b, the distal end 58 of the fastening device with the mounted mesh 252 is delivered to a surface 250 of a body tissue 256 at a site where the mesh 252 is to be fastened. Deployment of the fastener occurs by compressing the undeployed fastener to bring the crown 2 towards the baseplate 7. This is accomplished by depressing the trigger 60 towards the handle 52 of the fastening device 50. Squeezing the trigger 60 causes the pusher 62 to slide within a central lumen 59 of the shaft 54 of the fastening device. The pusher 62 urges the crown 2 towards the baseplate 7, while the baseplate 7 is immobilized by the radially inward projections 56, of the grippers 147 of the fastening device 50. FIG. 15c shows the partially deployed fastener 1. The prongs 5 of the fastener 1 have slid through the slots 8. The tips of the prongs 5 have penetrated through the mesh 252 into the tissue surface 250 and into the tissue 256. As deployment of the fastener continues, the prong tips develop a curved trajectory as they penetrate into the tissue to a specific predetermined depth and then move laterally, similar to the trajectory of a curved suturing needle within a tissue. The force necessary to fully spread the prongs 5 and deploy the fastener 1 is developed within the fastening device 50 between the pusher 59 and the projections 156 and is not applied to the tissue, thus preventing damage to the tissue such as tearing or perforating. The prongs 5 of the fastener 1 penetrate the tissue smoothly and attach the fastener to the tissue. Upon deployment of the fastener, the fastener becomes locked in its deployed configuration by engagement of the cantilevered beams 23 and 24 and the central bore 10.

Figure 15D:
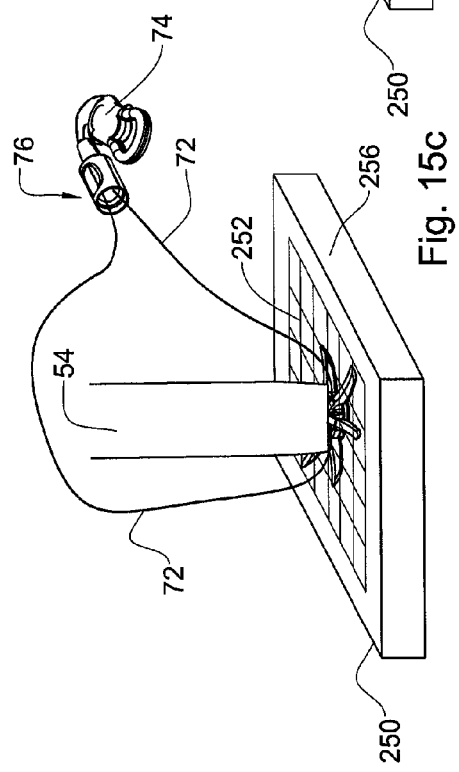

After deployment and fixation to the tissue and locking of the fastener in this deployed configuration, additional compression of the deployed fastener results in disengagement of the deployed fastener from the distal projections 56 of the grippers 47 and release of the fastener from the fastening device (FIG. 15d). In the deployed state, the crown 2 and the baseplate 7 remain on the tissue surface 250, and only the prongs 5 have penetrated into the tissue. If after deployment of the fastener 1, the location of the fastener 1 in the tissue 78 is satisfactory; the filament 72 can be cut and removed from the body together with the ring 74 and extraction device 76, as shown in FIG. 15d.

If the position of the fastener 1 in the tissue 256 is not satisfactory, the fastener 1 can be extracted from the tissue using an extraction device. In one embodiment, the extraction device 76, shown in FIG. 14 is used. The extraction device 76 is placed over the deployed fastener as shown in FIG. 16a.

The extraction device has an internal passageway shaft 346 that terminates in a lumen 344. The filament 72 passes along the lumen 344, passes through the fastener 1, and then returns through the lumen 344. The extraction device 76 is initially positioned with the prongs 5 abutted along a rim 345 of the lumen 344. The ring 72 is then pulled which pulls on the filament 72 which causes the crown 2 to be retracted into the lumen 344 of the extraction device 76, as shown in FIG. 16*b*. As the crown enters the lumen 344, the rim 345 presses downward on the splayed prongs 5 of the deployed fastener. The upward force on the crown 2 exerted by the filament 72 together with the downward force of the rim 345 on the prongs 5 causes the top element to unlatch from the baseplate 7. Continued pulling of the filament 72 draws the crown 2 into an upper chamber 347 of the lumen 344 (FIG. 16*c*). The relatively large dimensions of the baseplate 7 prevent the baseplate from entering the upper chamber 347 which becomes immobilized in a lower chamber 349 of the lumen 344 while the fastener 1 attains its undeployed configuration. The fastener 1 and extraction device 76 can then be removed from the body.

Figure 17A:
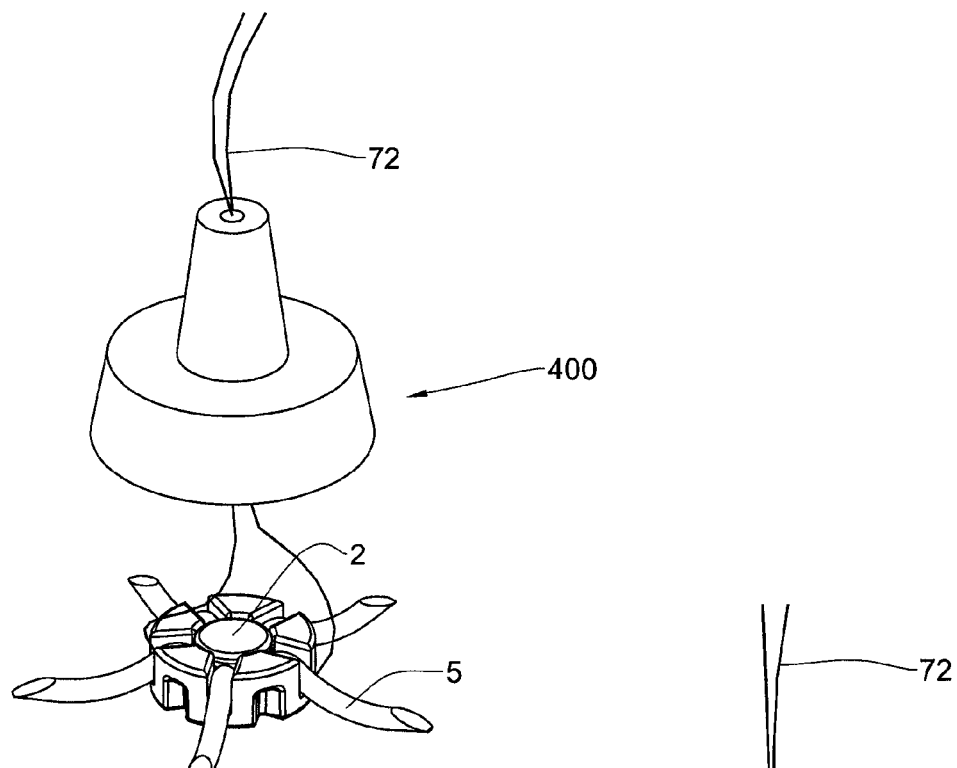
FIGS. 17a to 17c show extraction of a surgical fastener from a body tissue using a second embodiment of an extraction device.
Figure 17B:
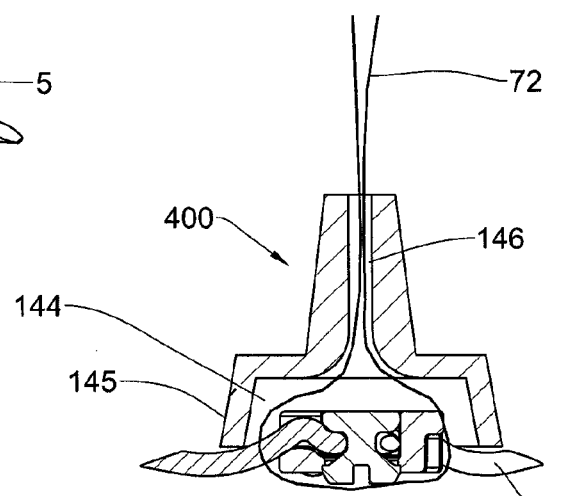
Figure 17C:
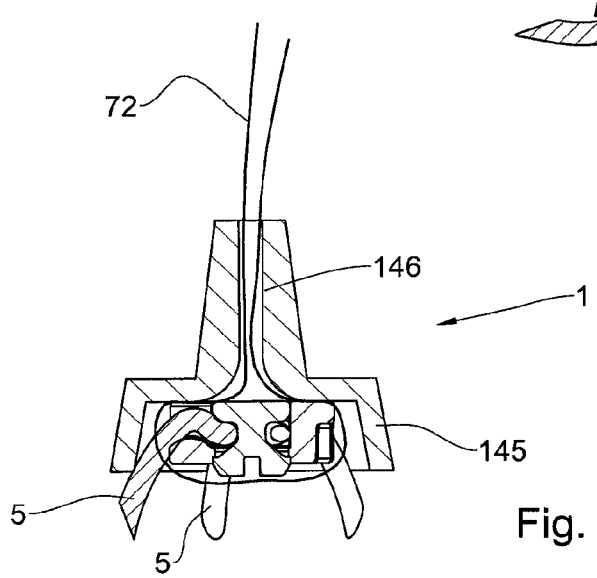

In another embodiment, an extraction device 400, shown in FIG. 17, is used instead of the extraction device 76. The extraction device 400 is placed over the deployed fastener 1 as shown in FIGS. 17*a* and 17*b*. The extraction device has an internal passageway shaft 146 that terminates in a lumen 144. The filament 72 passes along the lumen 144, passes through the fastener 1, and then returns through the lumen 144. The extraction device 76 is positioned with the crown 2 of the fastener 1 inside the interior lumen 144 of the extraction device. The ring 72 is then pulled and pulling the filament causes the crown 2 to be retracted into the lumen 144 of the extraction device. A rim 145 is abutted against the splayed prongs 5 of the deployed fastener. The filament 142 is then pulled while the rim 145 abuts against the prongs 5 (FIG. 16*c*). As the filament 142 continues to be pulled, the prongs 5 bend bringing the prong tips closer to the axis of the fastener (FIG. 16*c*), without separating the crown 1 from the baseplate 7. The fastener 1 and extraction device 400 can then be removed from the body.

The invention claimed is:

1. A surgical fastener having an undeployed configuration and a deployed configuration, the surgical fastener comprising:
   (a) a top element including a crown, and two or more prongs extending from the crown;
   (b) a baseplate having two or more slots, each slot being dimensioned to receive a tip of a prong of the top element in the undeployed configuration of the surgical fastener;
   wherein two or more cantilevered catches extend from the crown, each cantilevered catch terminating in a head;
   wherein the baseplate is provided with a central bore;
   wherein, in the deployed configuration, the heads pass through the central bore and latch the top element onto the baseplate;
   wherein, as the heads pass through the central bore, the two or more cantilevered catches are displaced inwards until the heads have completely passed through the central bore, and wherein the two or more cantilevered catches are then free to snap outwards to retain their original straight configuration;
   wherein in the undeployed configuration, the cantilevered catches do not latch the top element to the baseplate;
   wherein in the undeployed configuration, the cantilevered catches extend in a direction towards the baseplate; and
   wherein at least in the undeployed configuration, the cantilevered catches are encircled by the two or more prongs with respect to the crown.

2. The surgical fastener according to claim 1, wherein, in the undeployed configuration, each prong is immobilized in a slot by frictional forces between the prong and a wall of the slot, and wherein the prongs splay out radially upon when the fastener goes from the undeployed configuration to the deployed configuration.

3. The surgical fastener according to claim 1, wherein at least one of the heads is beveled.

4. The surgical fastener according to claim 1, wherein the crown has a shape of a disk, a rectangular or polygonal shape, or an irregularly shaped surface, wherein the baseplate has a shape of a disk, a rectangular, or polygonal shaped surface, or an irregularly shaped surface, and wherein the prongs have a rectangular profile, a round profile, an oval profile, a triangular profile, or an elliptical profile, and wherein the prongs have a blunt tip, a pointed tip or a barbed tip.

5. The surgical fastener according to claim 1, manufactured from a biodegradable material.

6. The surgical fastener according to claim 1, wherein the cantilevered catches extend from below the crown.

7. The surgical fastener according to claim 1, wherein the cantilevered catches are coextensive.

8. The surgical fastener according to claim 1, wherein said two or more slots extend from said central bore to an edge of said baseplate.

9. The surgical fastener according to claim 1, wherein in the undeployed configuration, the cantilevered catches extend in an axial direction towards the baseplate.

10. The surgical fastener according to claim 1, wherein said cantilevered catches are located inwardly of said two or more prongs with respect to the crown.

11. A system, comprising:
   one or more surgical fasteners, each surgical fastener having an undeployed configuration and a deployed configuration; and
   a surgical fastening device configured to bring each surgical fastener from the respective undeployed configuration to the respective deployed configuration;
   wherein each surgical fastener includes:
   (a) a top element including a crown, and two or more prongs extending from the crown;
   (b) a baseplate having two or more slots, each slot being dimensioned to receive a tip of a prong of the top element in the undeployed configuration of the fastener;
   wherein two or more cantilevered catches extend from the crown, each cantilevered catch terminating in a head;
   wherein the baseplate is provided with a central bore;
   wherein, in the deployed configuration, the heads pass through the central bore and latch the top element onto the baseplate;
   wherein, as the heads pass through the central bore, the cantilevered catches are displaced inwards until the heads have completely passed through the central bore, and wherein the cantilevered catches are then free to snap outwards to retain their original straight configuration;
   wherein, in the undeployed configuration, the catches do not latch the top element to the baseplate;
   wherein in the undeployed configuration, the cantilevered catches extend in a direction towards the baseplate; and wherein at least in the undeployed configuration, the cantilevered catches are encircled by the two or more prongs with respect to the crown.

12. The system according to claim 11, wherein the surgical fastening device comprises a shaft extending from a handle portion, the shaft having a distal end provided with radially inward projections.

13. The system according to claim 12, wherein the shaft of the surgical fastening device is detachable from the handle portion.

14. The system according to claim 12, wherein the shaft is provided with axial protrusions configured to grasp a mesh material.

15. The system according to claim 12, wherein the surgical fastening device further comprises a trigger and a pusher, and wherein squeezing the trigger against the handle portion causes the pusher to move distally inside a lumen of the shaft to eject a distal surgical fastener from the distal end of the shaft as the distal surgical fastener attains its deployed configuration.

16. The system according to claim 12, wherein the distal end of the shaft is configured to receive one of said one or more surgical fasteners that are loaded into a holder to form an assembly.

17. The system according to claim 12, further comprising:
a holder configured to be loaded with one of said one or more surgical fasteners to form the assembly; and
a cartridge configured to receive the assembly.

18. A system, comprising:
one or more surgical fasteners, each having an undeployed configuration and a deployed configuration;
(A) each said surgical fastener comprising:
  (a) a top element including a crown, and two or more prongs extending from the crown;
  (b) a base plate having two or more slots, each slot being dimensioned to receive a tip of a prong of the top element in the undeployed configuration of the fastener;
  wherein two or more cantilevered catches extend from the crown, each cantilevered catch terminating in a head;
  wherein the baseplate is provided with a central bore;
  wherein in the deployed configuration the heads pass through the central bore and latch the top element onto the baseplate;
  wherein, as the heads pass through the central bore, the cantilevered catches are displaced inwards until the heads have completely passed through the central bore, and wherein the cantilevered catches are then free to snap outwards to retain their original straight configuration;
  wherein in the undeployed configuration, the cantilevered catches do not latch the top element to the baseplate;
  wherein in the undeployed configuration, the cantilevered catches extend in a direction towards the baseplate; and
  wherein at least in the undeployed configuration, the cantilevered catches are encircled by the two or more prongs with respect to the crown;
a filament passing between the top element and the baseplate; and
(B) an extraction device having an internal passageway shaft that terminates in a lumen, the lumen being configured to receive the respective top element of a respective said surgical fastener, the lumen further having a rim dimensioned to allow the prongs of the respective said surgical fastener to abut the rim when the respective top element of the respective said surgical fastener is positioned in the lumen of the extraction device.

19. A method for extracting a surgical fastener that is affixed on a tissue surface, the surgical fastener having an undeployed configuration and a deployed configuration, and including:
(a) a top element including a crown, and two or more prongs extending from the crown;
(b) a baseplate having two or more slots, each slot being dimensioned to receive a tip of a prong of the top element in the undeployed configuration of the fastener;
wherein two or more cantilevered catches extend from the crown, each cantilevered catch terminating in a head;
wherein the baseplate is provided with a central bore;
wherein, in the deployed configuration, the heads pass through the central bore and latch the top element onto the baseplate;
wherein, as the heads pass through the central bore, the cantilevered catches are displaced inwards until the heads have completely passed through the central bore, and wherein the cantilevered catches are then free to snap outwards to retain their original straight configuration;
wherein, in the undeployed configuration, the cantilevered catches do not latch the top element to the baseplate;
wherein in the undeployed configuration, the cantilevered catches extend in a direction towards the baseplate; and
wherein at least in the undeployed configuration, the cantilevered catches are encircled by the two or more prongs with respect to the crown;
further comprising a filament passing between the top element and the baseplate;
the method comprising providing an upward force on the crown by the filament and providing a downward force on the prongs to cause the top element to unlatch from the baseplate.

20. The method according to claim 19, carried out by an extraction device having an internal passageway shaft that terminates in a lumen, the lumen being configured to receive the top element of said surgical fastener, the lumen further having a rim dimensioned to allow the prongs of said surgical fastener to abut the rim when the top element of said surgical fastener is positioned in the lumen of the extraction device.

* * * * *